United States Patent [19]

Mita et al.

[11] Patent Number: 4,780,561
[45] Date of Patent: Oct. 25, 1988

[54] PREPARATION PROCESS OF α-L-ASPARTYL-L-PHENYLALANINE METHYL ESTER OR HYDROCHLORIDE THEREOF

[75] Inventors: Ryuichi Mita, Kawasaki; Takeshi Oura, Zushi; Toshio Katoh, Kawasaki; Chojiro Higuchi; Akihiro Yamaguchi, both of Kamakura, all of Japan

[73] Assignee: Mitsui Toatsu Chemicals, Inc., Tokyo, Japan

[21] Appl. No.: 131,268

[22] Filed: Dec. 9, 1987

Related U.S. Application Data

[63] Continuation of Ser. No. 841,257, Mar. 19, 1986, abandoned.

[30] Foreign Application Priority Data

Mar. 29, 1985 [JP] Japan .................................. 60-66097
Apr. 1, 1985 [JP] Japan .................................. 60-66665

[51] Int. Cl.$^4$ .................. C07C 103/52; C07C 102/00
[52] U.S. Cl. ......................................... 560/40; 560/41; 530/801; 426/548
[58] Field of Search ................... 560/40, 41; 530/801; 549/253; 562/450; 426/548

[56] References Cited

U.S. PATENT DOCUMENTS 4,088,649  5/1978  Smith et al. .................... 544/385
4,634,790  1/1987  Shinohara et al. ................ 560/40

FOREIGN PATENT DOCUMENTS 1370    9/1971  Japan .
 82752    7/1978  Japan .
130846    7/1984  Japan .
225153   12/1984  Japan .

*Primary Examiner*—John Kight
*Assistant Examiner*—Nathan M. Nutter
*Attorney, Agent, or Firm*—Fisher, Christen & Sabol

[57] ABSTRACT

Disclosed herein is a process for preparing α-L-aspartyl-L-phenylalanine methyl ester or its hydrochloride from 5-benzyl-3,6-dioxo-2-piperazine acetic acid or its methyl ester, prepared without using L-penylalanine methyl ester which involves problems in its stability, as a raw material. Specifically, the process comprises: bringing 5-benzyl-3,6-dioxo-2-piperazine acetic acid in the presence of methanol or 5-benzyl-3,6-dioxo-2-piperazine acetic acid methyl ester in the presence or absence of methanol into contact with hydrochloric acid; isolating the thereby deposited α-L-aspartyl-L-phenylalanine methyl ester hydrochloride; and neutralizing said hydrochloride with an alkali as required. Preparation processes of 5-benzyl-3,6-dioxo-2-piperazine acetic acid or its methyl ester are also disclosed.

7 Claims, No Drawings

PREPARATION PROCESS OF α-L-ASPARTYL-L-PHENYLALANINE METHYL ESTER OR HYDROCHLORIDE THEREOF

This application is a continuation of application Ser. No. 841,257, filed 3/19/86, now abandoned.

This invention relates to a preparation process of α-L-aspartyl-L-phenylalanine methyl ester or its hydrochloride. More specifically, this invention relates to a process for preparing α-L-aspartyl-L-phenylalanine methyl ester or its hydrochloride which process comprises: bringing 5-benzyl-3,6-dioxo-2-piperazine acetic acid methyl ester in the presence or absence of methanol or 5-benzyl-3,6-dioxo-2-piperazine acetic acid in the presence of methanol into contact with hydrochloric acid so as to precipitate the thereby formed α-L-aspartyl-L-phenylalanine methyl ester in the form of its hydrochloride; isolating the α-L-aspartyl-L-phenylalanine methyl ester hydrochloride by solid-liquid separation; and neutralizing said hydrochloride with an alkali as required.

BACKGROUND OF THE INVENTION

α-L-aspartyl-L-phenylalanine methyl ester (hereinafter abbreviated as α-APM) is a useful substance as an artificial dipeptide sweetening agent. It has a sweetness approximately 200 times that of cane sugar as well as a similar sweet taste to cane sugar and is of low calory so that it is in ever-increasing demand as a diet sweetening agent.

Numerous preparation processes of α-APM have so far been disclosed. There may be cited a variety of processes, for example, (1) a process which comprises condensating the hydrochloride of aspartic acid anhydride with L-phenylalanine methyl ester (Japanese Patent Publication No. 40069/1976), (2) a process which comprises condensating N-protective aspartic acid anhydride with L-phenylalanine methyl ester followed by deprotection (Japanese Patent Laid-Open Nos. 1370/1971 and 113841/1976), (3) a process which comprises reacting N-protective aspartic acid-62 -benzyl ester with L-phenylalanine methyl ester in the presence of a condensating agent followed by de-protection (Japanese Patent Laid-Open No. 130846/1984) and (4) a process which comprises reacting N-carboxyaspartic acid anhydride with L-phenylalanine methyl ester (Japanese Patent Laid-Open No. 96557/1973).

However, all of these processes employ L-phenylalanine methyl ester as one of the raw materials, requiring complex steps of methyl-esterification of L-phenylalanine. Moreover, according to the investigations of the present inventors, it has been found that L-phenylalanine methyl ester is such a compound that its free two molecules are liable to condensate and cyclize to 2,5-dibenzyl-3,6-dioxo-piperazine in a solution and thus has problems in its stability. This fact is responsible for the various troubles occurring in its industrial production.

Accordingly, it is desirable to develop a process which is free of these disadvantages in the production of α-APM, i.e., a process in which other raw materials than L-phenylalanine methyl ester are used.

As a process for preparing α-APM which uses other raw materials than L-phenylalanine methyl ester, there have been disclosed a process for preparing α-APM which comprises condensating N-formyl aspartic acid anhydride with L-phenylalanine in glacial acetic acid to form N-formyl-α-L-aspartyl-L-phenylalanine, de-formylating the N-formyl-α-L-aspartyl-L-phenylalanine to form α-L-aspartyl-L-phenylalanine, and esterifying said compound in methanol (Japanese Patent Publication No. 26133/1980), and a process in which the esterification step of α-L-aspartyl-L-phenylalanine to α-APM in the above process is improved (Japanese Patent Laid-Open No. 82752/1978).

However, since the former process brings about the esterification reaction in a substantially non-aqueous solution, the reaction has practically no freedom of selectivity so that not only the intended esterification but also the esterification of the β-carboxyl group of aspartic acid as well as the diesterification takes place to a large extent. Therefore, the process suffers such disadvantages as low yields of α-APM.

The latter process brings about the esterification in the presence of water so as to increase the selectivity toward α-APM. However, the yield of isolation of α-APM is at most 50–60% based on α-L-aspartyl-L-phenylalanine and thus is insufficient.

As another process in which L-phenylalanine methyl ester is not used, there has recently been disclosed a process for preparing α-APM which comprises condensating the N-carboxylic acid anhydride of L-aspartic acid-β-methyl ester with L-phenylalanine to produce α-L-aspartyl L-phenylalanine-β-methyl ester and subjecting said compound to intramolecular transesterification in an aqueous hydrochloric acid solution containing methanol (Japanese Patent Laid-Open Nos. 225152/1984 and 225153/1984).

However, in this process, the esterification for producing the β-methyl ester of aspartic acid is poor in selectivity and thus is low in yield. Further, the N-carboxylic acid anhydride of aspartic acid-β-methyl ester, which is produced by reacting aspartic acid-β-methyl ester with phosgene, is liable to polymerize by being brought into contact with a base or other causes. Therefore, this process is disadvantageous from the industrial viewpoint.

As has been described above, the conventional preparation processes of α-APM have demerits in the stability of its intermediates, in yield or in safety. Thus, it is the existing state of art that there are no efficient processes for preparing α-APM.

SUMMARY OF THE INVENTION

An object of the present invention is to provide a process for preparing α-L-aspartyl-L-phenylalanine methyl ester or its hydrochloride from a compound, which can be prepared without using L-phenylalanine methyl ester which involves problems in its stability, as a raw material.

Another object of the present invention is to provide a process for preparing α-APM in an efficient manner by using, as a raw material, 5-benzyl-3,6-dioxo-2-piperazine acetic acid or 5-benzyl-3,6-dioxo-2-piperazine acetic acid methyl ester which has never been used as a raw material for the production of α-APM.

The present inventors have found that 5-benzyl-3,6-dioxo-2-piperazine acetic acid can be prepared efficiently by the de-formylation and diesterification of N-formyl-α-L-aspartyl-L-phenylalanine in methanol in the presence of an acid to form α-L-aspartyl-L-phenylalanine dimethyl ester and treating said diester with an aqueous alkaline solution.

The present inventors have also found that 5-benzyl-3,6-dioxo-2-piperazine acetic acid methyl ester can be prepared by the de-formylation and diesterification of N-formyl-α-L-aspartyl-L-phenylalanine in methanol in the presence of hydrogen chloride to form α-L-aspartyl-L-phenylalanine dimethyl ester and treating said diester under neutral or weakly alkaline conditions, for example, in a mixed solvent of water and methanol, and further 5-benzyl-3,6-dioxo-2-piperazine acetic acid is obtained by treating 5-benzyl-3,6-dioxo-2-piperazine acetic acid methyl ester with an alkali.

The present inventors have further found that 5-benzyl-3,6-dioxo-2-piperazine acetic acid methyl ester is also obtained by condensating and cyclizing the N-carboxylic acid anhydride of L-phenylalanine and L-aspartic acid dimethyl ester in an organic solvent, and 5-benzyl-3,6-dioxo-2-piperazine acetic acid is obtained by hydrolyzing 5-benzyl-3,6-dioxo-2-piperazine acetic acid methyl ester with an alkali, if necessary.

When 5-benzyl-3,6-dioxo-2-piperazine-2-acetic acid or its methyl ester is hydrolyzed with hydrochloric acid to open or cleave its two cyclic amide bonds, it should generally be assumed that α-L-aspartyl-L-phenylalanine and L-phenylalanine-L-aspartic acid as well as L-phenylalanine and L-aspartic acid formed by the cleavage of the two amido bonds are produced respectively in a large amount, thereby forming a complex reaction system, since no inherent difference is observed between the two amido bonds.

However, the present inventors have found that when 5-benzyl-3,6-dioxo-2-piperazine acetic acid in the presence of methanol or 5-benzyl-3,6-dioxo-2-piperazine acetic acid methyl ester in the presence or absence of methanol is brought into contact with hydrochloric acid under a mild condition, one of the two amido bonds in the molecule, which is going to be cleaved first, is cleaved relatively preferentially, leading to the direct formation of α-APM, and in the case of 5-benzyl-3,6-dioxo-2-piperadine acetic acid methyl ester, the hydrolysis of unnecessary ester group is caused to proceed simultaneously, thereby forming α-APM. Moreover, it has been found that by adjusting the concentration of hydrochloric acid during the reaction, the α-APM formed is precipitated out of the reaction system in the form of its hydrochloride, resulting in the production of α-APM in a good yield. The present invention has been completed on the basis of these findings.

Specifically, the present invention provides a process for preparing α-L-aspartyl-L-phenylalanine methyl ester or its hydrochloride which comprises: bringing 5-benzyl-3,6-dioxo-2-piperazine acetic acid methyl ester in the presence or absence of methanol or 5-benzyl-3,6-dioxo-2-piperazine acetic acid in the presence of methanol into contact with hydrochloric acid so as to precipitate α-APM hydrochloride; isolating the α-APM hydrochloride; and neutralizing said hydrochloride with an alkali as required. Preparation process of α-APM by the ring-opening of 5-benzyl-3,6-dioxo-2-piperazine acetic acid in the above-described manner is a novel process.

In accordance with the process of the present invention, (a) 5-benzyl-3,6-dioxo-2-piperazine acetic acid or its methyl ester to be used as a raw material can be prepared without using L-phenylalanine methyl ester which involves problems in its stability in a solution; and (b) the conversion of 5-benzyl-3,6-dioxo-2-piperazine acetic acid or its methyl ester to α-APM proceeds under a mild condition, thereby making it possible to produce α-APM in a good yield. In view of these advantages, the process of the present invention is a highly valuable preparation process of α-APM from the industrial standpoint.

DETAILED DESCRIPTION OF THE INVENTION

5-Benzyl-3,6-dioxo-2-piperazine acetic acid or its methyl ester which is used as a raw material in the process of the present invention can be prepared in the following manner:

(1) 5-benzyl-3,6-dioxo-2-piperazine acetic acid methyl ester can be prepared by condensating N-formyl-L-aspartic acid anhydride with L-phenylalanine to form N-formyl-α-L-aspartyl-L-phenylalanine, de-formylating and diesterifying the N-formyl-α-L-aspartyl-L-phenylalanine in methanol in the presence of an acid to produce α-L-aspartyl-L-phenylalanine dimethyl ester, and treating said diester, for example, in a mixed solvent of water and methanol under neutral or weakly alkaline conditions;

(2) 5-benzyl-3,6-dioxo-2-piperazine acetic acid methyl ester can be prepared by condensating and cyclizing the N-carboxylic acid anhydride of L-phenylalanine and L-aspartic acid dimehhyl ester in an organic solvent and/or water;

(3) 5-benzyl-3,6-dioxo-2-piperazine acetic acid can be prepared by hydrolyzing 5-benzyl-3,6-dioxo-2-piperazine acetic acid methyl ester, which is obtained in the above process (1) or (2), with an alkali; and (4) 5-benzyl-3,6-dioxo-2-piperazine acetic acid can be prepared by bringing α-L-aspartyl-L-phenylalanine dimethyl ester, which is obtained in the above process (1), into contact with an alkali.

These preparation processes are described more specifically hereinbelow.

(A) Preparation process of 5-benzyl-3,6-dioxo-2-piperazine acetic acid methyl ester The process (1) is a process in which the intended product is prepared by way of α-L-aspartyl-L-phenylalanine dimethyl ester from N-formyl-β-L-aspartyl-L-phenylalanine which is obtained by the condensation of N-formyl-L-aspartic acid anhydride and L-phenylalanine.

In this process, N-formyl-α-L-aspartyl-L-phenylalanine (which may contain the β-isomer, i.e., N-formyl-α-L-aspartyl-L-phenylalanine by-produced during the condensation) is de-formylated and diesterified in methanol in the presence of an acid to produce α-L-aspartyl-L-phenylalanine dimethyl ester, followed by the intramolecular cyclization of the α-L-aspartyl-L-phenylalanine dimethyl ester in a solvent under practically neutral or weakly alkaline conditions, thereby converting the diester to 5-benzyl-3,6-dioxo- 2-piperazine acetic acid methyl ester.

The step of preparing α-L-aspartyl-L-phenylalanine dimethyl ester from N-formyl-α-L-aspartyl-L-phenylalanine is carried out in such a manner that N-formyl-α-L-aspartyl-L-phenylalanine is fed into a methanol solution having an acid dissolved or an acid is added to a methanol solution having N-formyl-α-L-aspartyl-L-phenylalanine dissolved or suspended, and the resulting reaction mixture is reacted at 10°–70° C. for 0.5–50 hours or preferably at 20°–60° C. for 1–30 hours, whereby the N-formyl-α-L-aspartyl-L-phenylalanine is de-formylated and diesterified to form α-L-aspartyl-L-phenylalanine dimethyl ester.

The amount of methanol to be used is 20 parts by weight or less per part by weight of N-formyl-α-L- aspartyl-L-phenylalanine. The lower limit of the amount of methanol may be one part by weight per part by weight of N-formyl-α-L-aspartyl-L-phenylalanine from the operational viewpoint of the reaction.

As the acid, there may be mentioned inorganic acids such as hydrogen chloride, hydrogen bromide, sulfuric acid and phosphoric acid, aromatic sulfonic acids such as p-toluene sulfonic acid, chlorobenzene sulfonic acid and naphthalene sulfonic acid, and aliphatic sulfonic acids such as methane sulfonic acid and trifluoromethane sulfonic acid. Hydrogen chloride or sulfuric acid is frequently used on an industrial scale from the consideration of cost.

The amount of the acid to be used is one equivalent or more or preferably 1.1 equivalents or more relative to N-formyl-α-L-aspartyl-L-phenylalanine. No particular limitations are imposed on the upper limit of the amount of the acid to be used. However, its use in unduly excessive amounts may possibly cause the cleavage of peptide bond so that it is usually used in an amount of 5 equivalents or less relative to N-formyl-α-L-aspartyl-L-phenylalanine. If the amount is too small, the de-formylation and diesterification will not proceed satisfactorily.

The α-L-aspartyl-L-phenylalanine dimethyl ester formed in the foregoing manner is isolated from the reaction solution in the form of an acid adduct. Alternatively, the reaction solution containing α-L-aspartyl-L-phenylalanine dimethyl ester after having been removed methanol by distillation or the reaction solution as it is subjected to an intramolecular cyclization to form 5-benzyl-3,6-dioxo-2-piperazine acetic acid methyl ester.

The intramolecular cyclization of α-L-aspartyl-L-phenylalanine dimethyl ester to 5-benzyl-3,6-dioxo-2-piperazine acetic acid methyl ester is effected basically by treating α-L-aspartyl-L-phenylalanine dimethyl ester in an organic solvent and/or water with stirring under practically neutral or weakly alkaline conditions at a temperature in the range of from 10° C. to the boiling point of the solvent, preferably 20°–100° C.

Usable solvents are selected from any organic solvents which are inert to the cyclization reaction, in addition to water. Exemplary solvents may include alcohol solvents such as methanol, ethanol, propanol and butanol, hydrocarbon or halogenated hydrocarbon solvents such as benzene, toluene, xylene, methylene chloride, dichloroethane and chlorobenzene, ether solvents such as diethyl ether, diisopropyl ether, tetrahydrofuran and dioxane, keton solvents such as acetone, methyl ethyl ketone and diisobutyl ketone, ester solvents such as ethyl acetate and butyl acetate, glycol solvents such as ethylene glycol, ethylene glycol monomethyl ether and ethylene glycol monoethyl ether, nitrogen-containing solvents such as nitromethane, nitropropane, acetonitrile, formamide, acetoamide, N,N-dimethylformamide, N,N-dimethylacetoamide, pyridine, picoline, quinoline, N-methylpyrolidone and N,N'-dimethylimidazolidinone, and sulfur- or phosphorus-containing solvents such as carbon disulfide, dimethyl sulfoxide and phosphoric acid triester. As a matter of course, usable solvents are not limited to the above-described solvents. These solvents may be used either singly or in combination of two or more of them. They may also be used in the form of a mixed solvent with water. Among them, the use of methanol or a mixed solvent of methanol and water is particularly preferred.

Although no particular limitations are placed on the amount of the solvent to be used, it is recommended to use the solvent in an amount 50 times by weight or less that of α-L-aspartyl-L-phenylalanine dimethyl ester from the viewpoint of volume efficiency. The more preferred amounts are in the range of 1–30 times that of α-L-aspartyl-L-phenylalanine dimethyl ester.

In the preparation step of α-L-aspartyl-L-phenylalanine dimethyl ester from N-formyl-α-L-aspartyl-L-phenylalanine, the α-L-aspartyl-L-phenylalanine dimethyl ester is formed as an acid adduct. Consequently, the intramolecular cyclization of said diester to 5-benzyl-3,6-dioxo-2-piperazine acetic acid methyl ester is carried out under practically neutral or weakly alkaline conditions after its acid adduct and excess acid are neutralized with a suitable base so that α-L-aspartyl-L-phenylalanine dimethyl ester is made free substantially.

As the base useful for the neutralization, there may be cited inorganic bases such as hydroxides, oxides, carbonates and hydrogen carbonates of alkali or alkaline earth metals and ammonia, and organic bases such as triethylamine, pyridine and piperidine. When the intramolecular cyclization is carried out in water or in a mixed solvent of water and an organic solvent, the pH of the reaction liquid should be maintained below 11 or preferably in the range of 5–10. The base should thus be used so as not to cause the pH to exceed the above range.

5-Benzyl-3,6-dioxo-2-piperazine acetic acid methyl ester is formed in the above-described manner. 5-Benzyl-3,6-dioxo-2-piperazine acetic acid methyl ester is generally hardly soluble in solvents so that it is, in many cases, deposited as a precipitate out of the reaction system after the reaction. Accordingly, it can be isolated by solid-liquid separation after cooling the reaction liquid to room temperature or below, subsequent to the completion of the reaction and, if necessary, the concentration of the resulting reaction liquid.

The foregoing process (2) is a process in which the N-carboxylic acid anhydride of L-phenylalanine, which is obtained by reacting L-phenylalanine with phosgene, and L-aspartic acid dimethyl ester are condensated and cyclized. In this process, the N-carboxylic acid anhydride of L-phenylalanine and L-aspartic acid dimethyl ester are condensated at a molar ratio of about 1:1–1:2 in an organic solvent and/or water at a temperature in the range of from −40° to 40° C., preferably from −20° to 30° C. Therefor, the condensation product is treated, if necessary, with a basic substance, for example, a tertiary amine such as trimethylamine or pyridine, and a carbonate or hydrogen carbonate of an alkali or alkaline earth metal at a temperature in the range of from room temperature to the boiling point of the solvent in such a manner that the pH of the reaction liquid is not caused to exceed about 10. Thus, the intended 5-benzyl-3,6-dioxo-2-piperazine acetic acid methyl ester can be obtained. Various organic solvents which are basically the same as those employed in the aforesaid process (1) may be used as the organic solvent.

(B) Preparation process of
5-benzyl-3,6-dioxo-2-piperazine acetic acid

In the process (3), 5-benzyl-3,6-dioxo-2-piperazine acetic acid methyl ester prepared by the foregoing process (1) or (2) is hydrolyzed by bringing it into contact with a base such as the hydroxide, oxide or carbonate of an alkali or alkaline earth metal in water or in an organic solvent containing water. 5-Benzyl-3,6-dioxo-2-piperazine acetic acid is prepared by acidifying the resulting reaction liquid with an acid such as hydrochloric acid or sulfuric acid, after the removal or separation of the organic solvent by concentration, if necessary.

One equivalent or a little more of the base may be used satisfactorily relative to 5-benzyl-3,6-dioxo-2-piperazine acetic acid methyl ester. It is not necessary to use it in unduly excessive amounts. The temperature at which the ester is brought into contact with a base is in the range of 0°–100° C.; preferably 10°–80° C.

In the process (4), α-L-aspartyl-L-phenylalanine dimethyl ester prepared from N-formyl-α-L-aspartyl-L-phenylalanine in accordance with the foregoing process (1) is made free in water or an organic solvent containing water and then brought into contact with equivalent or a little more of the hydroxide, oxide or carbonate of an alkali or alkaline earth metal relative to the diester, thereby causing its intramolecular cyclization and the hydrolysis of ester group. 5-Benzyl-3,6-dioxo-2-piperazine acetic acid is prepared by acidifying the resulting liquid in the same manner as in the foregoing process (3).

No particular limitations are imposed on the kind and amount of the organic solvent to be used when the reaction is effected in the organic solvent containing water in each of the above two processes, so long as the organic solvent is stable to the base to be brought into contact with the ester or diester. Specifically, the majority of the organic solvents used in the process (1) may be used jointly with water except for the ester solvents. Since 5-benzyl-3,6-dioxo-2-piperazine acetic acid formed by the reaction is dissolved in the water layer as an alkali or alkaline earth metal salt when the organic solvent is immiscible with water, it is recovered by acidifying the water layer after the reaction mixture is fractionated into the organic layer and the water layer upon completion of the reaction.

5-Benzyl-3,6-dioxo-2-piperazine acetic acid and 5-benzyl-3,6-dioxo-2-piperazine acetic acid methyl ester obtained in the above-described manner are brought into contact respectively with hydrochloric acid which contains methanol and with hydrochloric acid which contains or does not contain methanol so as to prepare α-APM.

When 5-benzyl-3,6-dioxo-2-piperazine acetic acid is used as a raw material, methanol is used in an amount of 1–6 moles per mole of 5-benzyl-3,6-dioxo-2-piperazine acetic acid. When 5-benzyl-3,6-dioxo-2-piperazine acetic acid methyl ester is used as a raw material, methanol is used in an amount of 0–6 moles per mole of 5-benzyl-3,6-dioxo-2-piperazine acetic acid methyl ester. In other words, methanol may not be used in some cases.

If methanol is used in excess of 6 moles per mole of each of the raw materials, the concentration of methanol is increased in the reaction system so that the α-APM formed is dissolved to a greater extent and the further esterification of α-APM to α-L-aspartyl-L-phenylalanine dimethyl ester is unfavorably accelerated.

Hydrochloric acid is used in an amount of at least one mole or preferably 1–10 moles per mole of 5-benzyl-3,6-dioxo-2-piperazine acetic acid or its methyl ester. The concentration of hydrochloric acid to be used is in the range of 3–33% by weight, preferably 5–30% by weight.

If the concentration of hydrochloric acid is too low, it will become difficult to open or cleave the ring of 5-benzyl-3,6-dioxo-2-piperazine acetic acid or its methyl ester and therefore to obtain α-APM in a high yield. If the concentration of hydrochloric acid is excessively high, α-APM hydrochloride is made hard to deposit and besides side reactions are unfavorably induced.

A water-miscible organic solvent which is inert to the reaction and does not increase the solubility of α-APM in the reaction system may be added to the reaction system.

The temperature at which 5-benzyl-3,6-dioxo-2-piperazine acetic acid or its methyl ester is brought into contact with hydrochloric acid is in the range of from 0° C. to the boiling point of the reaction mixture, preferably 10°–60° C.

In this process, α-APM formed by the reaction is deposited out of the reaction system in the form of its hydrochloride. Therefore, α-APM hydrochloride is isolated by solid-liquid separation, after cooling the reaction mixture as required, subsequent to the completion of the reaction. α-APM hydrochloride thus isolated can be converted to free α-APM by neutralizing it in suspension or solution in water with a base such as sodium hydroxide, sodium carbonate, sodium hydrogen carbonate or ammonia.

The present invention is described more specifically with reference to the following examples.

EXAMPLE 1

To a solution containigg 27.4 g of hydrogen chloride dissolved in 600 ml of methanol was added 154 g of N-formyl-α-L-aspartyl-L-phenylalanine and the resulting mixture was reacted at room temperature for 24 hours. The reaction solution was concentrated under reduced pressure to distill off methanol.

The residue was dissolved in 200 ml of water and 50 ml of methanol and the resulting solution was added dropwise with a 20% aqueous sodium carbonate solution to adjust its pH at 7.2. The solution was stirred at room temperature for 24 hours. The precipitate thus deposited was filtered, washed with water and drived in vacuo to obtain a white crystal of 5-benzyl-3,6-dioxo-2-piperazine acetic acid methyl ester having a melting point of 217°–218° C. in an amount of 117.8 g.

A solution consisting of 12.8 g of methanol, 27.6 g of water and 39.6 g of conc. (35%) hydrochloric acid was heated to 50° C. To this solution was added little by little 27.6 g of the foregoing 5-benzyl-3,6-dioxo-2-piperazine acetic acid methyl ester for about one hour and the resulting mixture was reacted at 50°–60° C. for 3 hours. The reaction mixture was then cooled to room temperature at which it was reacted for 6 days. The reaction mixture was cooled with an ice water and was stirred at 3°–5° C. for 3 hours. A crystal of the α-APM hydrochloride thus deposited was filtered and washed with a cold water.

The crystal thus obtained was analyzed by high speed liquid chromatography, with the result that the crystal contained 17.9 g of α-APM formed in a yield of 60.9% based on 5-benzyl-3,6-dioxo-2-piperazine acetic acid methyl ester.

EXAMPLE 2

The α-APM hydrochloride obtained in Example 1 was suspended in 200 ml of water and to the suspension was added dropwise a 20% aqueous sodium carbonate solution at 20°–25° C. to neutralize it (pH=5.0). The resulting suspension was stirred at the same temperature for 30 minutes and then cooled to 5° C. at which it was further stirred for one hour. The crystal thereby deposited was filtered, washed with a cold water and dried in vacuo to obtain free α-APM in an amount of 16.4 g.

Its analysis by high speed liquid chromatography revealed that no impurities were detected in the α-APM. The specific rotation of the α-APM was as follows: $[\alpha]_D^{20} = 16.1°$ (C=4, 15N formic acid).

EXAMPLE 3

To a solution having 9.6 g of hydrogen chloride dissolved in 400 ml of methanol was fed 61.6 g of N-formyl-α-L-aspartyl-L-phenylalanine and the resulting mixture was reacted at 50°-60° C. for 6 hours. The reaction solution was cooled to 10° C., added dropwise with 105.6 g of a 10% aqueous sodium hydroxide solution and then subjected to reaction at 30°-40° C. for 20 hours. Thereafter, the reaction mixture was cooled to 5° C. and the crystal thereby deposited was filtered, washed with methanol and water and dried to obtain 37.6 g of 5-benzyl-3,6-dioxo-2-piperazine acetic acid methyl ester having a melting point of 216°-217.5° C.

To a solution consisting of 6.4 g of methanol, 12.5 g of water and 31.3 g of conc. hydrochloric acid was added 27.6 g of the obtained 5-benzyl-3,6-dioxo-2-piperazine acetic acid methyl ester at 50°-55° C. for about one hour. The resulting mixture was reacted at the same temperature for 4 hours and then cooled to 30° C. at which it was further reacted for 5 days. Thereafter, the reaction mixture was treated in the same manner as described in Example 1, thereby isolating α-APM hydrochloride in a yield of 63.1% based on 5-benzyl-3,6-dioxo-2-piperazine acetic acid methyl ester.

EXAMPLE 4

To a solution having 9.6 g of hydrogen chloride dissolved in 400 ml of methanol was fed 61.6 g of N-formyl-α-L-aspartyl-L-phenylalanine and the resulting mixture was reacted at 50°-60° C. for 6 hours. The resulting reaction solution was cooled to room temperature, added dropwise with 30.4 g of triethylamine, and then subjected to further reaction under reflux for 8 hours. The reaction mixture was cooled to room temperature and the crystal thereby deposited was filtered and washed with methanol to obtain 40.2 g of 5-benzyl-3,6-dioxo-2-piperazine acetic acid methyl ester having a melting point of 216°-218° C.

To a solution consisting of 4.8 g of methanol, 27.8 g of water and 20.9 g of conc. hydrochloric acid was fed 27.6 g of the obtained 5-benzyl 3,6-dioxo-2-piperazine acetic acid methyl ester at 55°-60° C. for about 2 hours and the resulting mixture was reacted at the same temperature for 4 hours. Then, the reaction mixture was cooled to room temperature at which it was further reacted for 7 days. After the reaction, the reaction mixture was treated in the same manner as described in Example 1, so that α-APM hydrochloride was isolated in a yield of 53.8% based on 5-benzyl-3,6-dioxo-2-piperazine acetic acid methyl ester.

EXAMPLE 5

The procedure of Example 3 was repeated except that 25.0 g of methane sulfonic acid was used in place of 9.6 g of hydrochloric acid and the reaction temperature and time of the de-formylation and diesterification were respectively changed to 40°-45° C. and 6 hours, thereby obtaining 38.6 g of 5-benzyl-3,6-dioxo-2-piperazine acetic acid methyl ester.

Then, 27.6 g of the obtained 5-benzyl-3,6-dioxo-2-piperazine acetic acid methyl ester was treated under the same conditions for producing α-APM hydrochloride as described in Example 3, thereby obtaining α-APM hydrochloride in a yield of 58.3% based on 5 benzyl-3,6-dioxo-2-piperazine acetic acid methyl ester.

EXAMPLE 6

To a solution containing 11.6 g of hydrogen chloride dissolved in 400 ml of methanol was fed 61.6 g of N-formyl-α-L-aspartyl-L-phenylalanine and the resulting mixture was reacted at 40°-45° C. for 6 hours. Then, the resulting solution was distilled under reduced pressure to remove methanol. The residue was dissolved in 100 ml of dioxane and 200 ml of water. A 20% aqueous sodium carbonate solution was added dropwise to the resulting solution so as to adjust its pH at 7.8 and thereafter further reaction was conducted at 40°-45° C. for 20 hours. Then, the reaction mixture was cooled to room temperature and the crystal thereby deposited was filtered, washed with dioxane and then with water, and dried to obtain 40.6 g of 5-benzyl-3,6-dioxo-2-piperazine acetic acid methyl ester.

Then, 27.6 g of the obtained 5-benzyl-3,6-dioxo-2-piperazine acetic acid methyl ester was treated under the same conditions for producing α-APM hydrochloride as described in Example 4, thereby obtaining α-APM hydrochloride in a yield of 51.6% based on 5-benzyl-3,6-dioxo-2-piperazine acetic acid methyl ester.

EXAMPLE 7

In 1,500 ml of acetonitrile was suspended 49.5 g of L-aspartic acid dimethyl ester hydrochloride, to which 25.5 g of triethylamine was added dropwise. Thereafter, the resulting mixture was stirred at room temperature for one hour and the triethylamine hydrochloride thus deposited was filtered. The resulting solution of L-aspartic acid dimethyl ester in acetonitrile was cooled to 5° C., to which 48.0 g of the N-carboxylic acid anhydride of L-phenylalanine was added little by little at temperatures below 5° C. for about one hour. Then, the resulting mixture was further reacted at 5° C. for 25 hours. The reaction liquid was raised in temperature to room temperature. Then, triethylamine was added to the reaction liquid to render it basic. The resulting liquid was subjected to reaction at room temperature for 24 hours. The crystal thereby deposited was filtered, washed with acetonitrile and then with water, and dried in vacuo at 50° C. to obtain 32.0 g of a white crystal of 5-benzyl-3,6-dioxo-2-piperazine acetic acid methyl ester. This crystal was recrystallized from a 50% aqueous methanol solution to obtain a purified product having a melting point of 217°-218° C.

Then, 27.6 g of the obtained 5-benzyl-3,6-dioxo-2-piperazine acetic acid methyl ester was treated under the same conditions for producing α-APM hydrochloride as described in Example 1, thereby obtaining α-APM hydrochloride in a yield of 55.7% based on 5-benzyl-3,6-dioxo-2-piperazine acetic acid methyl ester.

EXAMPLE 8

In 1,000 l of a 50% aqueous methanol solution was suspended 55 g of the 5-benzyl-3,6-dioxo-2-piperazine acetic acid methyl ester obtained in Example 1, and 42 g of a 20% aqueous sodium hydroxide solution was added to the suspension at room temperature under stirring. Then, the hydrolysis was conducted at room temperature for two hours to form an aqueous solution. Thereafter, conc. hydrochloric acid was added dropwise to the aqueous solution, which had been removed with methanol under reduced pressure by distillation, to adjust its pH at 1. The resulting mixture was stirred at room temperature for one hour and the crystal thereby deposited was filtered, washed with water and dried to obtain 5-benzyl-3,6-dioxo-2-piperazine acetic acid.

Then, 26.2 g of the thus obtained 5-benzyl-3,6-dioxo-2-piperazine acetic acid was fed into a solution consisting of 12.8 g of methanol, 27.6 g of water and 39.6 g of conc. hydrochloric acid at 50°–60° C. for about one hour, and the resulting mixture was stirred at the same temperature for 3 hours. Then, the mixture was cooled to room temperature at which it was further reacted for 7 days. After the reaction, the reaction mixture was cooled with an ice water and stirred at 3°–5° C. for 3 hours. The crystal of α-APM hydrochloride thus dposited was filtered and washed with a cold water.

The crystal thus obtained was analyzed by high speed liquid chromatography, with the result that it contained 17.3 g of α-APM formed in a yield of 58.8% based on 5-benzyl-3,6-dioxo-2-piperazine acetic acid.

EXAMPLE 9

The α-APM hydrochloride obtained in Example 8 was dissolved under heating in 200 ml of water, to which sodium hydrogen carbonate was added little by little for neutralization (pH=5.0). Then, the reaction mixture was cooled to 5° C. at which it was stirred for one hour. The crystal thereby deposited was filtered, washed with a cold water and dried in vacuo to obtain 15.3 g of free α-APM.

Its analysis by high speed liquid chromatography revealed that no impurities were detected in the α-APM. The specific rotation of the α-APM was as follows: $[\alpha]_D^{20} = 16.13°$ (C=4, 15N formic acid).

EXAMPLE 10

Into a solution consisting of 6.4 g of methanol, 27.6 g of water and 39.6 g of conc. hydrochloric acid was charged 26.2 g of the 5-benzyl-3,6-dioxo-2-piperazine acetic acid obtained in the manner as described in Example 8 at 50°–60° C. for about one hour, and the resulting mixture was stirred at the same temperature for 3 hours. Then, the mixture was cooled to 30° C. at which it was further reacted for 6 days. After the reaction, the resulting mixture was treated in the same manner as described in Example 1 to obtain α-APM hydrochloride in a yield of 51.8% based on 5-benzyl-3,6-dioxo-2-piperazine acetic acid.

EXAMPLE 11

Into a solution containing 27.4 g of hydrogen chloride dissolved in 600 ml of methanol was charged 154 g of N-formyl-α-L-aspartyl-L-phenylalanine, and the resulting mixture was reacted at room temperature for 24 hours. The reaction solution was concentrated under reduced pressure to distil off methanol. The residue was dissolved in 500 ml of water and 500 ml of methanol, and the resulting solution was neutralized with a 20% aqueous sodium hydroxide solution. Then, 120 g of a 20% aqueous sodium hydroxide solution was added dropwise to the solution at room temperature for about two hours, and the resulting solution was subjected to further reaction at room temperature for 3 hours. Thereafter, methanol was distilled off under reduced pressure, and conc. hydrochloric acid was added dropwise to the resulting aqueous solution until its pH reached 1. The resulting mixture was stirred at room temperature for one hour and the crystal thereby deposited was filtered, washed with water and dried to obtain 93.4 g of a white crystal of 5-benzyl-3,6-dioxo-2-piperazine acetic acid.

By using 26.2 g of the 5-benzyl-3,6-dioxo-2-piperazine acetic acid thus obtained, the reaction was carried out in the same manner as described in Example 8 except that the amounts of methanol, water and conc. hydrochloric acid were respectively changed to 16.0 g, 33.1 g and 31.3 g, thereby obtaining α-APM hydrochloride in a yield of 59.3% based on 5-benzyl-3,6-dioxo-2-piperazine acetic acid.

What is claimed is:

1. A process for preparing α-L-aspartyl-L-phenylalanine methyl ester or hydrochloride thereof which process comprises: bringing 5-benzyl-3,6-dioxo-2-piperazine acetic acid methyl ester in the presence or absence of methanol into contact with hydrochloric acid; isolating the thereby deposited α-L-aspartyl-L-phenylalanine methyl ester hydrochloride; and neutralizing said hydrochloride with an alkali as required.

2. A process for preparing α-L-aspartyl-L-phenylalanine methyl ester or hydrochloride thereof which process comprises: bringing 5-benzyl-3,6-dioxo-2-piperazine acetic acid methyl ester into contact with hydrochloric acid in the presence of 0–6 moles of methanol per mole of 5-benzyl-3,6-dioxo-2-piperazine acetic acid methyl ester; isolating the thereby deposited α-L-aspartyl-L-phenylalanine methyl ester hydrochloride; and neutralizing said hydrochloride with an alkali as required.

3. A process as claimed in claim 1 wherein the concentration of hydrochloric acid is in the range of 3–33% by weight.

4. A process as claimed in claim 1 wherein hydrochloric acid is used in an amount of 1–10 moles per mole of 5-benzyl-3,6-dioxo-2-piperazine acetic acid or methyl ester thereof used as a raw material.

5. A process as claimed in claim 1 wherein the temperature of the contact is in the range of from 0° C. to the boiling point of the reaction mixture.

6. A process as claimed in claim 1 wherein 5-benzyl-3,6-dioxo-2-piperazine acetic acid methyl ester is obtained by de-formylating and diesterifying N-formyl-α-L-aspartyl-L-phenylalanine in methanol in the presence of an acid to produce α-L-aspartyl-L-phenylalanine dimethyl ester followed by the intramolecular cyclization of said diester in water and/or an organic solvent under neutral or weakly alkaline conditions.

7. A process as claimed in claim 1 wherein 5-benzyl-3,6-dioxo-2-piperazine acetic acid methyl ester is the one obtained by condensating and the cyclizing the N-carboxylic acid anhydride of L-phenylalanine with L-aspartic acid dimethyl ester in an organic solvent and/or water.

* * * * *